United States Patent [19]
Imashiro et al.

[11] Patent Number: 6,121,406
[45] Date of Patent: Sep. 19, 2000

[54] MIXTURE OF HYDROPHILIC DICYCLOHEXYLMETHANECARBODIIMIDE

[75] Inventors: Yasuo Imashiro; Ikuo Takahashi; Yoshihiro Yamazaki, all of Tokyo, Japan

[73] Assignee: Nisshinbo Industries, Inc., Tokyo, Japan

[21] Appl. No.: 09/292,005

[22] Filed: Apr. 15, 1999

[30] Foreign Application Priority Data

Apr. 20, 1998 [JP] Japan ................................. 10-109238

[51] Int. Cl.[7] .......................... C08G 73/00; C08G 18/00; C08L 79/00
[52] U.S. Cl. ............................. 528/170; 528/44; 528/48; 528/51; 528/59; 528/67; 524/710; 524/792; 524/793; 524/873
[58] Field of Search ................................. 528/44, 51, 59, 528/48, 67, 170; 524/792, 710, 793, 873

[56] References Cited

U.S. PATENT DOCUMENTS

| | | |
|---|---|---|
| 5,338,794 | 8/1994 | Imashiro et al. .......................... 524/792 |
| 5,373,080 | 12/1994 | Imashiro et al. ............................ 528/67 |

*Primary Examiner*—P. Hampton-Hightower
*Attorney, Agent, or Firm*—Kubovcik & Kubovcik

[57] ABSTRACT

A hydrophilic dicyclohexylmethanecarbodiimide represented by the formula (1):

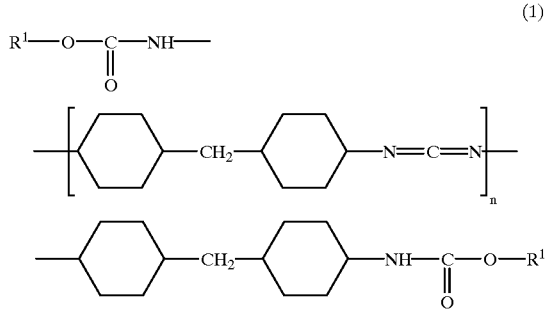

wherein n is an integer of 1 to 10 and $R^1$ is a residue of a mixture of organic compounds of different hydrophilicities each having at least one hydroxyl group capable of reacting with an isocyanate group. The hydrophilic dicyclohexylmethanecarbodiimide is improved in reactivity and storage stability, and is thereby easy to handle as a crosslinking agent for hydrophilic resins.

5 Claims, No Drawings

MIXTURE OF HYDROPHILIC DICYCLOHEXYLMETHANECARBODIIMIDE

BACKGROUND OF THE INVENTION (1). Field of the Invention

The present invention relates to a novel hydrophilic carbodiimide. More particularly, the present invention relates to a hydrophilic dicyclohexylmethanecarbodiimide which is improved in reactivity and storage stability and thereby is easy to handle as a crosslinking agent for hydrophilic resins.

(2). Description of the Prior Art

Hydrophilic resins are in use in many applications such as coatings, inks, textile treatment agents, adhesives and the like. They, however, are in inferior to lipophilic resins in water resistance because they have hydrophilicity.

To improve the water resistance of a hydrophilic resin, it has been conducted to use a crosslinking agent together with the resin. As the crosslinking agent, there is used a compound having a methylol group, ethyleneimine group, epoxy group, isocyanate group or the like.

Some of such conventional crosslinking agents are excellent in imparting water resistance of hydrophilic resins. In recent years, hydrophilic resins have come to be used in wider applications and more excellent properties are required. In many cases, hydrophilic resins are required to have crosslinkability at low to ordinary temperature. Hydrophilic resins are also required to have good storage stability after the crosslinking agents are mixed thereinto, and no hazardous effects to human, and so on. The above crosslinking agents, however, are not fully effective when used in hydrophilic resins at low to ordinary temperature, and incapable of giving hydrophilic resins sufficient water resistance, and, moreover, they are not sufficiently safe in view of the hazard to human health (skin stimulation etc.).

Recently, attention has been paid to those carbodiimide compounds which are used in amidation between carboxyl group and amino group, peptide synthesis from amino acid, etc., because such carbodiimide compounds can act as a crosslinking agent for hydrophilic resin and have high safety.

With respect to the technique of using a carbodiimide compound as a crosslinking agent, there are disclosed a polycarbodiimide derived from isophorone diisocyanate and a method for crossliking of hydrophilic resins using the polycarbodiimide, in, for example, JP-A-59-187029 and JP-B-5-27450.

In the above method, the crosslinking of a hydrophilic resin is conducted by utilization of a reaction between the carbodiimide group of a polycarbodiimide and the active hydrogen of an active hydrogen compound, for example, a reaction between the carbodiimide group of a polycarbodiimide and the carboxylic group contained in a hydrophilic acrylic resin.

The above-mentioned carbodiimide compound derived from isophorone diisocyanate, however, is highly reactive and has had problems in that (1) the storage stability after addition to a hydrophilic resin is low because of the high reactivity and (2) the time from addition to the hydrophilic resin, to application of the mixture is short.

In JP-A-7-330849 is described a carbodiimide compound derived from tetramethylxylylene diisocyanate, which has good storage stability after addition to a hydrophilic resin. In this carbodiimide compound derived from tetramethylxylylene diisocyanate, the reactivity of the carbodiimide group is low and, therefore, the storage stability of the compound after addition to a hydrophilic resin is superior to that of the carbodiimide compound derived from isophorone diisocyanate. In using the carbodiimide compound derived from tetramethylxylylene diisocyanate, however, a long time is taken for the crosslinking and there are cases that no sufficient effect is obtained when the crosslinking is conducted at low temperatures and in a short time.

As a carbodiimide compound capable of exhibiting a sufficient effect in crosslinking at low temperatures and in a short time, there is disclosed, in JP-A-10-30024, a multi-branching type carbodiimide compound having four or more branches each having a carbodiimide group. This multi-branching type carbodiimide compound, as compared with straight-chain carbodiimide compounds, can give a high crosslink density even in the crosslinking at low temperatures and short time; however, the compound has no good storage stability after addition to a hydrophilic resin and its storage period is shorter than that of straight-chain carbodiimide compounds.

SUMMARY OF THE INVENTION

In view of the above situation, the present invention has an object of providing a hydrophilic dicyclohexylmethanecarbodiimide which is improved in reactivity and storage stability and thereby is easy to handle as a crosslinking agent for hydrophilic resins.

The present inventors made a study in order to achieve the above object. As a result, the present inventors found out that when an organic compound of high hydrophilicity and an organic compound of low hydrophilicity are used in combination to obtain a hydrophilic carbodiimide compound, the organic compound of low hydrophilicity protects the carbodiimide group which reacts with the functional group (e.g. carboxyl group) contained in the hydrophilic resin; as a result, when the resulting carbodiimide compound is added to a hydrophilic resin, the reactivity of the carbodiimide compound with the functional group (e.g. carboxyl group) contained in the hydrophilic resin can be reduced; consequently, the carbodiimide compound has significantly improved storage stability despite the high reactivity, as compared with conventional hydrophilic carbodiimide compounds. The present invention has been completed based on the above finding.

According to the present invention there is provided a hydrophilic dicyclohexylmethanecarbodiimide represented by the following general formula (1):

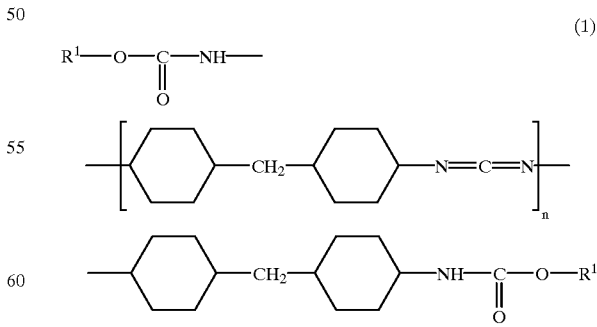

wherein n is an integer of 1 to 10 and $R^1$ is a residue of a mixture of organic compounds of different hydrophilicities each having at least one hydroxyl group capable of reacting with isocyanate group.

DETAILED DESCRIPTION OF THE INVENTION

The present invention is hereinafter described in detail.

The hydrophilic carbodiimide compound of the present invention is represented by the above general formula (1) and is obtained by a reaction of an isocyanate-terminated dicyclohexylmethanecarbodiimide obtained from 4,4'-dicyclohexylmethane diisocyanate

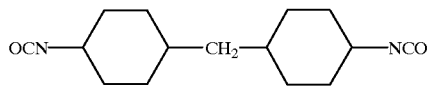

with a mixture of organic compounds of different hydrophilicities each having at least one hydroxyl group capable of reacting with an isocyanate group.

In the above general formula (1), n represents an integer of 1 to 10.

The hydrophilic carbodiimide compound of the present invention having the above-mentioned feature can be produced specifically by subjecting the above 4,4'-dicyclohexylmethane diisocyanate to a condensation reaction where carbon dioxide is removed, to form an isocyanate-terminated dicyclohexylmethanecarbodiimide and then reacting this carbodiimide with a mixture of organic compounds of different hydrophilicities each having at least one hydroxyl group capable of reacting with isocyanate group.

The formation of the isocyanate-terminated dicyclohexylmethanecarbodiimide can be conducted based on conventional processes for polycarbodiimide production (see U.S. Pat. No. 2,941,956; JP-B-47-33279; J. Org. Chem., 28, 2069 to 2076 (1963); Chemical Review 1981, Vol. 81, No. 4,619–4,621).

The condensation reaction of the dicyclohexylmethane diisocyanate where carbon dioxide is removed, proceeds in the presence of a carbodiimidization catalyst. As the catalyst, there can be used, for example, a phosphorene oxide such as 1-phenyl-2-phosphorene-1-oxide, 3-methyl-2-phosphorene-1-oxide, 1-5 ethyl-2-phosphorene-1-oxide, 1-ethyl-3-methyl-2-phosphorene-1-oxide, 3-methyl-1-phenyl-2-phosphorene-1-oxide, 3-phosphorene isomer thereof, or the like. Of these, 3-methyl-1-phenyl-2-phosphorene-1-oxide is preferred in view of the reactivity.

The reaction temperature of the condensation reaction is preferably about 80 to 180° C. When the reaction temperature is lower than the range, a very long reaction time is required; when the reaction temperature is higher than the range, side reactions take place and it is impossible to obtain a carbodiimide of good quality; therefore, neither case is preferred.

The condensation degree of the isocyanate-terminated dicyclohexylmethanecarbodiimide is preferably 1 to 10. When the condensation degree is higher than 10, the dispersibility of the hydrophilic dicyclohexylmethanecarbodiimide added to a hydrophilic resin is low; and a uniform solution or dispersion of the hydrophilic dicyclohexylmethanecarbodiimide could not be obtained owing to the low dispersibility. To complete the condensation reaction as quickly as possible, it is preferred to conduct the reaction in a current of an inert gas such as nitrogen or the like.

As the organic compounds having at least one hydroxyl group capable of reacting with an isocyanate group, various organic compounds can be used. As the organic compound of high hydrophilicity, there can be mentioned, for example, a poly(ethylene oxide) having an alkoxy-blocked terminal, represented by the following general formula (2):

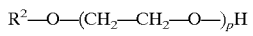

(wherein p is an integer of 4 to 30 and $R^2$ is a lower alkyl group). Specific examples thereof are a poly(ethylene oxide) monomethyl ether and a poly(ethylene oxide) monoethyl ether. A poly(ethylene oxide) monomethyl ether is particularly preferred. Incidentally, in the present specification, the term "lower" refers to 1 to 5 carbon atoms.

As the organic compound of low hydrophilicity having at least one hydroxyl group capable of reacting with an isocyanate group, there can be mentioned, for example, a poly(alkylene oxide) having an alkoxy-blocked terminal, represented by the following general formula (3):

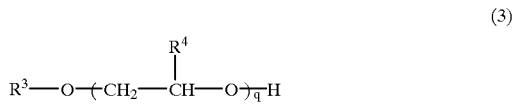

(wherein q is an integer of 1 to 3; $R^3$ is a lower alkyl group or a phenyl group; and $R^4$ is a lower alkyl group). Specific examples thereof are a poly(propylene oxide) monomethyl ether, a poly(propylene oxide) monoethyl ether and a polypropylene oxide) monophenyl ether. A poly(propylene oxide) monomethyl ether is particularly preferred.

As the organic compound of low hydrophilicity having at least one hydroxyl group capable of reacting with an isocyanate group, there can also be mentioned, for example, a dialkylaminoalcohol represented by the following general formula (4):

(wherein $R^5$ is a lower alkyl group and $R^6$ is a hydrogen atom or a lower alkyl group). Specific examples thereof are 3-dimethylamino-1-propanol, 3-diethylamino-1-propanol and 1-diethylamino-2-propanol. 1-diethylamino-2-propanol is particularly preferred.

In the present invention, the mixture of organic compounds of different hydrophilicities each having at least one hydroxyl group capable of reacting with an isocyanate group, is preferably a mixture containing an organic compound of high hydrophilicity and an organic compound of low hydrophilicity at a molar ratio of 1:1 to 1:19. When the molar ratio of the two organic compounds is outside of this range, for example, when the proportion of the organic compound of low hydrophilicity is lower than specified, the protection of the carbodiimide group by the organic compound of low hydrophilicity is not sufficient; and when the resulting hydrophilic dicyclohexylmethanecarbodiimide is added to a hydrophilic resin, the reaction of the carbodiimide compound with the functional group (e.g. carboxyl group) contained in the hydrophilic resin proceeds and the resultant mixed solution has low storage stability. When only the organic compound of low hydrophilicity is used, the dispersibility of the hydrophilic dicyclohexylmethanecarbodiimide added to a hydrophilic resin is low; and a uniform solution or dispersion of the hydrophilic dicyclohexylmethanecarbodiimide can not be obtained owing to the low dispersibility.

The addition reaction of the isocyanate-terminated dicyclohexylmethanecarbodiimide with the mixture of organic compounds of different hydrophilicities each having at least one hydroxyl group capable of reacting with an isocyanate group may be conducted using a catalyst, but the reaction proceeds easily only by heating.

The reaction temperature of the above reaction is about 60 to about 160° C., preferably about 100 to about 150° C.

When the reaction temperature is lower than the range, a very long reaction time is required; when the reaction temperature is higher than the range, side reactions take place and it is impossible to obtain a hydrophilic carbodiimide of good quality; therefore, neither case is preferred.

The hydrophilic dicyclohexylmethanecarbodiimide of the present invention can be isolated from the reaction system by an ordinary method. That the compound has a structure represented by the general formula (1) can be confirmed by its IR absorption spectrum or NMR absorption spectrum.

The hydrophilic dicyclohexylmethanecarbodiimide produced as above can be used in various forms. When added to a hydrophilic resin or the like, it may be added thereto as it is; however, addition in the form of an aqueous solution or dispersion is preferred for easy mixing.

Incidentally, the term "hydrophilic" used for the present dicyclohexylmethanecarbodiimide means that the compound is water-soluble or self-emulsifiable, has sufficient compatibility with water, and can form a uniform solution or emulsion with water.

EXAMPLES

The present invention is described in more detail below by way of Examples.

Example 1

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an was slowly added 1,052 g of distilled water to obtain a light yellow transparent carbodiimide solution (resin concentration=0% by weight).

Example 2

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 145.5 g of a poly(ethylene oxide) monomethyl ether having a condensation degree p of about 12 and 55.6 g of propylene glycol monomethyl ether (their molar ratio in mixture=3:7). The resulting mixture was subjected to a reaction at 150° C. for 5 hours. After the reaction, the reaction mixture was cooled to 80° C. Thereto obtain an emulsive carbodiimide solution (resin concentration=0% by weight).

Example 3

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 48.5 g of a poly(ethylene oxide) monomethyl ether having a condensation degree p of about 12 and 71.4 g of propylene glycol monomethyl ether (their molar ratio in mixture=1:9). The resulting mixture was subjected to a reaction at 150° C. for 5 hours. After the reaction, the reaction mixture was cooled to 80° C. Thereto was slowly added 930 g of distilled water to obtain an emulsive carbodiimide solution (resin concentration=40% by weight).

Example 4

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 48.5 g of a poly(ethylene oxide) monomethyl ether having a condensation degree p of about 12 and 117.5 g of dipropylene glycol monomethyl ether (their molar ratio in mixture=1:9). The resulting mixture was subjected to a reaction at 150° C. for 5 hours. After the reaction, the reaction mixture was cooled to 80° C. Thereto was slowly added 999 g of distilled water to obtain an emulsive carbodiimide solution (resin concentration=40% by weight).

Example 5

Synthesis of hydrophilic dicyclohexylmethanecarbodiimide 578 g of 4,41-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 48.5 g of a poly(ethylene oxide) monomethyl ether having a condensation degree p of about 12 and 163.5 g of tripropylene glycol monomethyl ether (their molar ratio in mixture=1:9). The resulting mixture was subjected to a reaction at 150° C. for hours. After the reaction, the reaction mixture was cooled to 80° C. Thereto was slowly added 1,068 g of distilled water to isocyanate-terminated dicyclohexylmethanecarbodiimide (condensation degree=4). To the isocyanate-terminated dicyclohexylmethanecarbodiimide was added a mixture of 242.5 g of a poly(ethylene oxide) monomethyl ether having a condensation degree p of about 12 and 39.7 g of propylene glycol monomethyl ether (their molar ratio in mixture=1:1). The resulting mixture was subjected to a reaction at 150° C. for 5 hours. After the reaction, the reaction mixture was cooled to 80° C. Thereto was slowly added 1,173 g of distilled water to obtain a light yellow transparent carbodiimide solution (resin concentration=40% by weight).

Example 6

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 48.5 g of a poly(ethylene oxide) monomethyl ether having a condensation degree p of about 12 and 120.6 g of propylene glycol monophenyl ether (their molar ratio in mixture=1:9). The resulting mixture was subjected to a reaction at 150° C. for 5 hours. After the reaction, the reaction mixture was cooled to 80° C. Thereto was slowly added 1,004 g of distilled water to obtain an emulsive carbodiimide solution (resin concentration=40% by weight).

Example 7

Synthesis of hydrophilic dicyclohexylmethanecarbodiimide 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 242.5 g of a poly(ethylene oxide) monomethyl ether having a condensation degree p of about 12 and 57.8 g of N,N-diethylisopropanolamine (their molar ratio in mixture=1:1). The resulting mixture was subjected to a reaction at 150° C. for 5 hours. After the reaction, the reaction mixture was cooled to 80° C. Thereto was slowly added 1,200 g of distilled water to obtain a light yellow transparent carbodiimide solution (resin concentration=40% by weight).

Example 8
Synthesis of hydrophilic dicyclohexylmethanecarbodiimide
578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminate dicyclohexylmethanecarbodiimide was added a mixture of 145.5 g of a poly(ethylene oxide) monomethyl ether having a condensation degree p of about 12 and 80.9 g of N,N-diethylisopropanol-amine (their molar ratio in mixture=3:7). The resulting mixture was subjected to a reaction at 150° C. for 5 hours. After the reaction, the reaction mixture was cooled to 80° C. Thereto was slowly added 1,080 g of distilled water to obtain a light yellow transparent carbodiimide solution (resin concentration=40% by weight).

Example 9
Synthesis of hydrophilic dicyclohexylmethanecarbodiimide
5 578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added a mixture of 48.5 g of a poly(ethylene oxide) monomethyl ether having a condensation degree p of about 12 and 104.0 g of N,N-diethylisopropanolamine (their molar ratio in mixture=1:9). The resulting mixture was subjected to a reaction at 150° C. for 5 hours. After the reaction, the reaction mixture was cooled to 80° C. Thereto was slowly added 979 g of distilled water to obtain an emulsive carbodiimide solution (resin concentration=40% by weight).

Example 10
Synthesis of hydrophilic dicyclohexylmethanecarbodiimide
584 g of 4,4'-dicyclohexylmethane diisocyanate was reacted with 2.9 g of 3-methyl-1-phenyl-2-phosphorene-1-oxide carbodiimidization catalyst) at 180° C. for 17 hours to obtain an isocyanate-terminated dicyclohexylmethanecarbodiimide (condensation degree=6). To the isocyanate-terminated dicyclohexylmethanecarbodiimide was added a mixture of 242.5 g of a poly(ethylene oxide) monomethyl ether having a condensation degree p of about 12 and 39.7 g of propylene glycol monomethyl ether (their molar ratio in mixture=1:1). The resulting mixture was subjected to a reaction at 150° C. for 5 hours. After the reaction, the reaction mixture was cooled to 80° C. Thereto was slowly added 1,173 g of distilled waster to obtain an emulsive carbodiimide solution (resin concentration=40% by weight).

Example 11
Synthesis of hydrophilic dicyclohexylmethanecarbodiimide
589 g of 4,4'-dicyclohexylmethane diisocyanate was reacted with 3.0 g of 3-methyl-1-phenyl-2-phosphorene-1-oxide (a carbodiimidization catalyst) at 180° C. for 21 hours to obtain an isocyanate-terminated dicyclohexylmethanecarbodiimide (condensation degree=9). To the isocyanate-terminate dicyclohexylmethanecarbodiimide was added a mixture of 242.5 of a poly(ethylene oxide) monomethyl ether having a condensation degree p of about 12 and 39.7 g of propylene glycol monomethyl ether (their molar ratio in mixture=1:1). The resulting mixture was subjected to a reaction at 150° C. for 5 hours. After the reaction, the reaction mixture was cooled to 80° C. Thereto was slowly added 1,173 g of distilled waster to obtain an emulsive carbodiimide solution (resin concentration=40% by weight)

Comparative Example 1
Synthesis 1 of hydrophilic dicyclohexylmethanecarbodiimide
578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added 485.0 g of a poly(ethylene oxide) monomethyl ether having a condensation degree P of about 12. The resulting mixture was subjected to a reaction at 150° C. for 5 hours. After the reaction, the reaction mixture was cooled to 50° C. Thereto was slowly added 1,478 g of distilled water to obtain a light yellow transparent carbodiimide solution (resin concentration=40% by weight).

Comparative Example 2
Synthesis of hydrophilic isophoronecarbodiimide
594 g of isophorone diisocyanate was reacted with 2.9 g of 3-methyl-1-phenyl-2-phosphorene-1-oxide (a carbodiimidization catalyst) at 180° C. for 10 hours to obtain a isocyanate-terminated isophoronecarbodiimide (condensation degree=4). To the isocyanate-terminated isophoronecarbodiimide was added 588.8 g of a poly(ethylene oxide) monomethyl ether having a condensation degree P of about 12. The resulting mixture was subjected to a reaction at 150° C. for 5 hours. After the reaction, the reaction mixture was cooled to 50° C. Thereto was slowly added 1,633 g of distilled waster to obtain a light yellow transparent carbodiimide solution (resin concentration=5 40% by weight).

Comparative Example 3
Synthesis of hydrophilic tetramethylxylylenecarbodiimide
584 g of m-tetramethylxylylene diisocyanate was reacted with 11.7 g of 3-methyl-1-phenyl-2-phosphorene-1-oxide (a carbodiimidization catalyst) at 180° C. for 20 hours to obtain an isocyanate-terminated tetramethylxylylenecarbodiimide (condensation degree=4). To the isocyanate-terminated tetramethylxylylenecarbodiimide was added 526.8 g of a poly(ethylene oxide) monomethyl ether having a condensation degree P of about 12. The resulting mixture was subjected to a reaction at 150° C. for 6 hours. After the reaction, the reaction mixture was cooled to 50° C. Thereto was slowly added 1,558 g of distilled water to obtain a light yellow-amber transparent carbodiimide solution (resin concentration=40% by weight).

Comparative Example 4
Synthesis 2 of hydrophilic dicyclohexylmethanecarbodiimide
578 g of 4,4'-dicyclohexylmethane diisocyanate was reacted with 2.9 g of 3-methyl-1-phenyl-2-phosphorene-1-oxide (a carbodiimidization catalyst) at 180° C. for 15 hours to obtain an isocyanate-terminated dicyclohexylmethanecarbodiimide (condensation degree=4). To the isocyanate-terminated dicyclohexylmethanecarbodiimide was added 79.4 g of propylene glycol monomethyl ether. The resulting mixture was subjected to a reaction at 150° C. for 5 hours. After the reaction, the reaction mixture was cooled to 50° C. Thereto was slowly added 869 g of distilled waster so that the resin concentration in the resulting mixture became 40% by weight. Agglomeration of carbodiimide resin occurred and it was impossible to obtain a uniform carbodiimide solution. The obtained carbodiimide resin per se was added to a hydrophilic resin, but the carbodiimide resin caused agglomeration, making it impossible to obtain a uniform mixture.

Reference Example 1

Storage stabilities 1 of hydrophilic dicyclohexylmethanecarbodiimides when added to hydrophilic resin Each of the hydrophilic dicyclohexylmethanecarbodiimide solutions obtained in Examples 1 to 9 was mixed with carboxyl group-containing urethane type hydrophilic resin (acid value=30mgKOH/g, resin concentration=33% by weight) so that the carbodiimide group and the carboxyl group became 1:1 in equivalent. The mixed solution was measured for viscosity change at 25° C. For comparison, the same test was conducted for each of the hydrophilic carbodiimide solutions obtained in Comparative Examples 1 to 3. The test results are shown in Table 1.

TABLE 1

| Hydrophilic carbodi-imide | Storage period | | | | | | |
|---|---|---|---|---|---|---|---|
| | Right after mixing | 1 day | 3 day | 7 day | 14 day | 28 day | 42 day |
| Example 1 | 290 cp | 205 cp | 193 cp | 195 cp | 247 cp | 290 cp | 373 cp |
| Example 2 | 277 cp | 198 cp | 151 cp | 166 cp | 198 cp | 244 cp | 321 cp |
| Example 3 | 252 cp | 181 cp | 140 cp | 156 cp | 183 cp | 221 cp | 269 cp |
| Example 4 | 271 cp | 197 cp | 160 cp | 170 cp | 197 cp | 227 cp | 284 cp |
| Example 5 | 291 cp | 196 cp | 154 cp | 171 cp | 193 cp | 237 cp | 309 cp |
| Example 6 | 260 cp | 183 cp | 147 cp | 162 cp | 188 cp | 219 cp | 280 cp |
| Example 7 | 333 cp | 244 cp | 209 cp | 226 cp | 248 cp | 271 cp | 303 cp |
| Example 8 | 319 cp | 208 cp | 153 cp | 160 cp | 168 cp | 189 cp | 200 cp |
| Example 9 | 315 cp | 197 cp | 122 cp | 125 cp | 131 cp | 140 cp | 167 cp |
| Example 10 | 295 cp | 297 cp | 201 cp | 210 cp | 260 cp | 305 cp | 365 cp |
| Example 11 | 308 cp | 221 cp | 230 cp | 235 cp | 307 cp | 340 cp | 411 cp |
| Comparative Example 1 | 572 cp | 599 cp | 647 cp | Gelation | | | |
| Comparative Example 2 | 583 cp | 708 cp | Gelation | | | | |
| Comparative Example 3 | 343 cp | 361 cp | 395 cp | 477 cp | 543 cp | 689 cp | Gelation |

Reference Example 2

Crosslinking abilities 1 of hydrophilic dicyclohexylmethanecarbodiimides

Each of the hydrophilic dicyclohexylmethanecarbodiimde solutions obtained in Examples 1 to 9 was mixed with a carboxyl group-containing urethane type hydrophilic resin (to which a blue pigment had been added) (acid value= 30mgKOH/g, resin concentration=33% by weight) so that the carbodiimide group and the carboxyl group became 1:1 in equivalent. The mixed solution was casted on a polyethylene terephthalate film (thickness=100 μm), followed by drying at 80° C. for 20 minutes to form a coating film having an as-dried thickness of about 30 μm. The surface of the coating film was rubbed with a solvent-infiltrated absorbent cotton (the solvent is shown below) to examine the times of rubbing needed for the absorbent cotton to become blue or for the coating film to be peeled. For comparison, the same test was conducted for each of the hydrophilic carbodiimide solutions obtained in Comparative Examples 1 to 3. The test results are shown in Table 2.

Solvent 0.28% ammonia waster waster/methanol mixed solvent (mixing ratio: waster/methanol=4/6 in weight)

Ethyl acetate

TABLE 2

| Hydrophilic carbodiimide | Solvent resistance test (times of rubbing) | | |
|---|---|---|---|
| | 0.28% ammonia water | Water/methanol | Water/methanol |
| Example 1 | More than 100 | More than 100 | 17 |
| Example 2 | More than 100 | More than 100 | 16 |
| Example 3 | More than 100 | More than 100 | 25 |
| Example 4 | More than 100 | More than 100 | 15 |
| Example 5 | More than 100 | More than 100 | 19 |
| Example 6 | More than 100 | More than 100 | 20 |
| Example 7 | More than 100 | More than 100 | 17 |
| Example 8 | More than 100 | More than 100 | 19 |
| Example 9 | More than 100 | More than 100 | 23 |
| Example 10 | More than 100 | More than 100 | 17 |
| Example 11 | More than 100 | More than 100 | 21 |

TABLE 2-continued

| Hydrophilic carbodiimide | Solvent resistance test (times of rubbing) | | |
|---|---|---|---|
| | 0.28% ammonia water | Water/methanol | Water/methanol |
| Comparative Example 1 | More than 100 | More than 100 | 17 |
| Comparative Example 2 | More than 100 | More than 100 | 19 |
| Comparative Example 3 | 69 | 25 | 8 |
| No addition | 58 | 18 | 8 |

Reference Example 3
Storage stabilities 2 of hydrophilic dicyclohexylmethanecarbodiimides when added to hydrophilic resin 6 g of each of the hydrophilic dicyclohexylmethanecarbodiimide solutions obtained in Examples 1 to 9 was mixed with 100 g of a carboxyl group-containing acrylic type hydrophilic resin used in textile printing inks. The mixed solution was measured for viscosity change at 40° C. For comparison, the same test was conducted for each of the hydrophilic carbodiimide solutions obtained in Comparative Examples 1 to 3. The test results are shown in Table 3.

TABLE 3

| Hydrophilic carbodiimide | Storage period | | | | | | |
|---|---|---|---|---|---|---|---|
| | Right after mixing | 1 hour | 3 hour | 6 hour | 9 hour | 12 hour | 15 hour |
| Example 1 | 455 cp | 455 cp | 491 cp | 552 cp | 590 cp | 631 cp | 680 cp |
| Example 2 | 487 cp | 471 cp | 502 cp | 517 cp | 592 cp | 619 cp | 663 cp |
| Example 3 | 484 cp | 468 cp | 484 cp | 520 cp | 528 cp | 532 cp | 539 cp |
| Example 4 | 524 cp | 525 cp | 517 cp | 581 cp | 591 cp | 617 cp | 630 cp |
| Example 5 | 527 cp | 529 cp | 536 cp | 599 cp | 610 cp | 634 cp | 660 cp |
| Example 6 | 498 cp | 485 cp | 491 cp | 520 cp | 536 cp | 544 cp | 556 cp |
| Example 7 | 548 cp | 369 cp | 374 cp | 341 cp | 362 cp | 370 cp | 408 cp |
| Example 8 | 558 cp | 496 cp | 468 cp | 470 cp | 626 cp | 525 cp | 548 cp |
| Example 9 | 486 cp | 445 cp | 477 cp | 445 cp | 450 cp | 483 cp | 540 cp |
| Example 10 | 462 cp | 470 cp | 488 cp | 543 cp | 587 cp | 635 cp | 690 cp |
| Example 11 | 471 cp | 482 cp | 487 cp | 550 cp | 609 cp | 673 cp | 688 cp |
| Comparative Example 1 | 540 cp | 624 cp | 727 cp | Gelation | | | |
| Comparative Example 2 | 591 cp | 730 cp | Gelation | | | | |
| Comparative Example 3 | 522 cp | 539 cp | 538 cp | 547 cp | 560 cp | 571 cp | 589 cp |

Reference Example 4
Crosslinking abilities 2 of hydrophilic Dicyclohexylmethanecarbodiimides 6 g of each of the hydrophilic dicyclohexylmethanecarbodiimide solutions obtained in Examples 1 to 9 was mixed with 100 g of a carboxyl group-containing acrylic type hydrophilic resin used in textile printing inks. The mixed solution was casted on a polyethylene terephthalate film (thickness=100 μm), followed by drying at 80° C. for 5 minutes and then at 130° C. for 2 minutes to form a coating film having an as-dried thickness of about 50 μm. The surface of the coating film was rubbed with a waster-infiltrated absorbent cotton to examine the times of rubbing up to when the base material (the polyethylene terephthalate film) became visible. For comparison, the same test was conducted for each of the hydrophilic carbodiimide solutions obtained in Comparative Examples 1 to 3. The test results are shown in Table 4.

TABLE 4

| Hydrophilic carbodiimide | Water resistance test (times of rubbing) |
|---|---|
| Example 1 | 4 |
| Example 2 | 11 |
| Example 3 | 13 |
| Example 4 | 8 |
| Example 5 | 8 |
| Example 6 | 10 |
| Example 7 | 4 |
| Example 8 | 5 |
| Example 9 | 6 |
| Example 10 | 6 |

TABLE 4-continued

| Hydrophilic carbodiimide | Water resistance test (times of rubbing) |
|---|---|
| Example 11 | 9 |
| Comparative Example 1 | 3 |
| Comparative Example 2 | 4 |
| Comparative Example 3 | 5 |
| No addition | 3 |

As is clear from Tables 1 to 4, the hydrophilic dicyclohexylmethanecarbodiimides of the present invention, as compared with other hydrophilic carbodiimides, are superior in storage stability when added to a hydrophilic resin and have high reactivity; therefore, can act as an excellent crosslinking agent for hydrophilic resin.

What is claimed is:

1. A mixture of hydrophilic dicyclohexylmethanecarbodiimides represented by the formula (1):

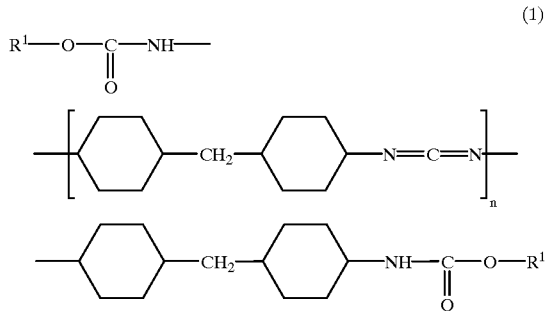

wherein n is an integer of 1 to 10 and $R^1$ is a residue of a hydrophilic organic compound having at least one hydroxyl group reactive with an isocyanate group, said mixture being obtained by the reaction of an isocyanate-terminated dicyclohexylmethanecarbodiimide obtained from 4,4'-dicyclohexylmethane diisocyanate with a mixture of organic compounds of different hydrophilicities.

2. The mixture of hydrophilic dicyclohexylmethanecarbodiimides according to claim 1 wherein the mixture of organic compounds of different hydrophilicities is a mixture of a poly(ethylene oxide) having an alkoxy-blocked terminal, represented by the formula (2):

$$R^2-O-(CH_2-CH_2-O-)_pH \qquad (2)$$

wherein p is an integer of 4 to 30 and $R^2$ is a lower alkyl group;

and a poly(alkylene oxide) having an alkoxy-blocked terminal, represented by the formula (3):

$$R^3-O-(CH_2-\underset{\underset{R^4}{|}}{CH}-O)_q H \qquad (3)$$

wherein q is an integer of 1 to 3; $R^3$ is a lower alkyl group or a phenyl group; and $R^4$ is a lower alkyl group.

3. The mixture of hydrophilic dicyclohexylmethanecarbodiimides according to claim 1 wherein the mixture of organic compounds of different hydrophilicities is a mixture of a poly(ethylene oxide) having an alkoxy-blocked terminal, represented by the formula (2):

$$R^2-O-(CH_2-CH_2-O-)_pH \qquad (2)$$

wherein p is an integer of 4 to 30 and $R^2$ is a lower alkyl group;

and a dialkylaminoalcohol represented by the formula (4):

$$(R^5)_2-N-CH_2-CHR^6-OH \qquad (4)$$

wherein $R^5$ is a lower alkyl group and $R^6$ is a hydrogen atom or a lower alkyl group.

4. The mixture of hydrophilic dicyclohexylmethanecarbodiimide according to claim 2, wherein the molar ratio of the poly(ethylene oxide) having an alkoxy-blocked terminal, represented by the formula (2) and the poly(alkylene oxide) having an alkoxy-blocked terminal, represented by the formula (3) is 1:1 to 1:19.

5. The mixture of hydrophilic dicyclohexylmethanecarbodiimide according to claim 3, wherein the molar ratio of the poly(ethylene oxide) having an alkoxy-blocked terminal, represented by the formula (2) and the dialkylaminoalcohol represented by the formula (4) is 1:1 to 1:19.

* * * * *